United States Patent [19]

Connor et al.

[11] 4,107,429

[45] Aug. 15, 1978

[54] **1-NOR-2-AMINO CARBAMATES DERIVED FROM ACID S, AN ANTIBIOTIC PRODUCED BY *POLYANGIUM CELLULOSUM* VAR. *FULVUM***

[75] Inventors: David T. Connor, Parsippany; Samuel M. Ringel; Maximilian von Strandtmann, both of Rockaway, all of N.J.

[73] Assignee: Warner-Lambert Company, Morris Plains, N.J.

[21] Appl. No.: 765,569

[22] Filed: Feb. 4, 1977

Related U.S. Application Data

[63] Continuation-in-part of Ser. No. 696,096, Jun. 14, 1976, abandoned.

[51] Int. Cl.[2] .............................................. C09B 23/00

[52] U.S. Cl. .................................... 542/447; 424/115; 424/121; 424/122

[58] Field of Search .................... 260/240 R; 424/115, 424/121, 122; 542/447

[56] References Cited

U.S. PATENT DOCUMENTS

| | | | |
|---|---|---|---|
| 3,651,216 | 3/1972 | Ringel et al. | 424/115 |
| 3,804,948 | 4/1974 | Strandtmann et al. | 424/122 |
| 4,001,398 | 1/1977 | Connor et al. | 424/122 |
| 4,009,261 | 2/1977 | Connor et al. | 424/122 |
| 4,016,257 | 4/1977 | Connor et al. | 424/122 |

*Primary Examiner*—Paul F. Shaver
*Attorney, Agent, or Firm*—Albert H. Graddis; Frank S. Chow; Anne M. Kelly

[57] ABSTRACT

The present invention relates to 1-nor-2-amino carbamates derived from the antibiotic substance, designated acid S, produced by *Polyangium cellulosum* var. *fulvum* (ATCC No. 25532), and to processes for their production. The 1-nor-2-amino carbamates of acid S of this invention are useful as antifungal agents.

11 Claims, 6 Drawing Figures

1-NOR-2-AMINODIOL S ETHYL CARBAMATE

1-NOR-2-AMINODIOL S
METHYL CARBAMATE

1-NOR-2-AMINODIOL S
ISOPROPYL CARBAMATE

1-NOR-2-AMINODIOL S
n-PROPYL CARBAMATE

1-NOR-2-AMINODIOL S
ETHYL CARBAMATE DIACETATE

1-NOR-2-AMINO CARBAMATES DERIVED FROM ACID S, AN ANTIBIOTIC PRODUCED BY *POLYANGIUM CELLULOSUM* VAR. *FULVUM*

CROSS REFERENCE TO RELATED APPLICATION

This application is a continuation-in-part of co-pending U.S. Application Ser. No. 696,096 filed June 14, 1976, now abandoned.

SUMMARY OF THE INVENTION

The present invention relates to novel 1-nor-2-amino carbamates derived by structurally modifying substance known as acid S, a potent antibiotic isolated from *Polyangium cellulosum* var. *fulvum* (ATCC No. 25532). Specifically, the present invention relates to 1-nor-2-amino carbamates derived from acid S, and having the formula:

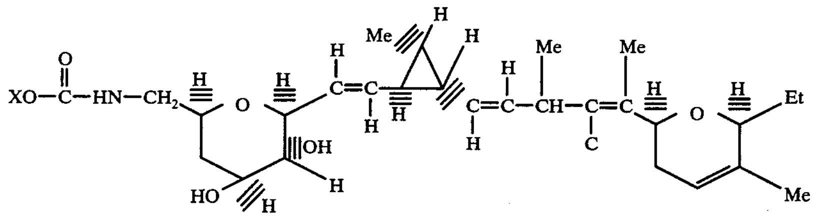

wherein X is a 1 to 7 carbon straight or branched chain alkyl group (preferably 1 to 4 carbon atoms), with the proviso that the 4 carbon alkyl group is n-butyl, isobutyl or secondary butyl. The 1-nor-2-amino carbamates of acid S are prepared by the reaction of acid S with diphenylphosphonic azide and triethylamine in t-butanol to obtain the corresponding diol S-1-one-1-azide which is then reacted with appropriate lower alkyl alcohol to form the desired 1-nor-2-aminodiol S alkyl carbamates of the invention.

BRIEF DESCRIPTION OF THE DRAWINGS

The infrared spectra of representative derivatives of acid S of this invention are illustrated in FIGS. 1, 2, 3, 4, 5 and 6 of the drawings.

The novel 1-nor-2-amino carbamates of acid S of this invention have the formula I:

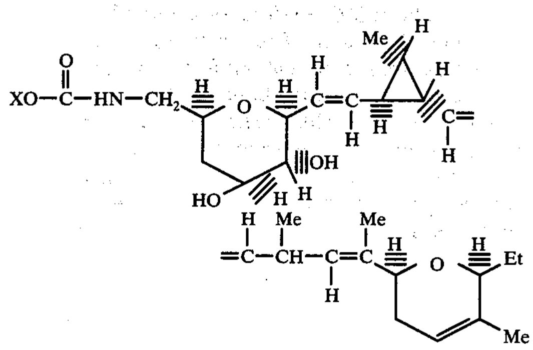

I wherein X is a 1 to 7 carbon straight or branched chain alkyl group, preferably 1 to 4 carbon atoms, with the proviso that the 4 carbon alkyl group is n-butyl, isobutyl or secondary butyl. The acid S molecule has the empirical formula $C_{28}H_{42}O_6$ and may be represented by the formula II:

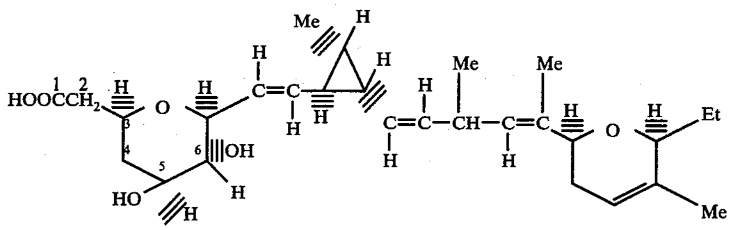

II

Thus the 1-nor-2-amino carbamates of this invention are derivatives of the acid function of the acid S molecule.

Acid S, as disclosed in U.S. Pat. No. 3,651,216, issued Mar. 21, 1972 and U.S. Pat. No. 3,804,948, issued Apr. 16, 1974, has the following characteristics:

Empirical Formula $C_{28}H_{42}O_6$, MW 474, infrared spectrum $\nu$ 870, 965, 1063, 1255, 1388, 1453, 1663, 1710, 2950, and 3400 cm.$^{-1}$, approximate $[\alpha]_D25$ + 36°, (chloroform, C = 0.7), Rf 0.56 [silica gel, ethyl acetate:isopropanol: water (85:10 :5)].

Acid S is a potent antifungal substance, elaborated when the microorganism *Polyangium cellulosum var. fulvum* (ATCC No. 25532) is fermented in a suitable culture medium.

The organism designated *Polyangium cellulosum var. fulvum* is deposited at the American Type Culture Collection, and identified as ATCC No. 25532. All restriction on the availability of the culture deposit at ATCC will be irrevocably removed upon issuance of the instant application. The culture at ATCC will be maintained throughout the effective life of the patent.

According to the subject invention, 1-nor-2-amino carbamates (I) of acid S are prepared by reacting 1-equivalent of acid S (II) with from about 2.5 to 3 equivalents of diphenylphosphonic azide and about 2.5 to 3 equivalents of triethylamine in a sufficient amount of t-butanol to maintain reflux action. Typically, from about 100 to about 300 (preferably about 150) equivalents of t-butanol are used. The reaction is conducted at reflux temperature for from about five to about twenty-four hours, preferably for about six hours, until the reaction is complete. Yields are improved if the reaction is conducted in an inert atmosphere, i.e., under nitrogen, but this is not critical. The product of aforementioned reaction, designated Diol S-1-one-1-Azide has an empirical formula $C_{28}H_{41}N_3O_5$ and may be represented by the formula III:

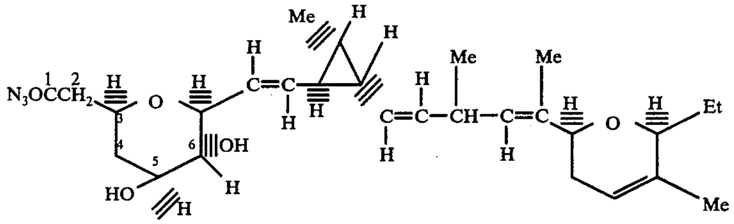

III

Figure 1:
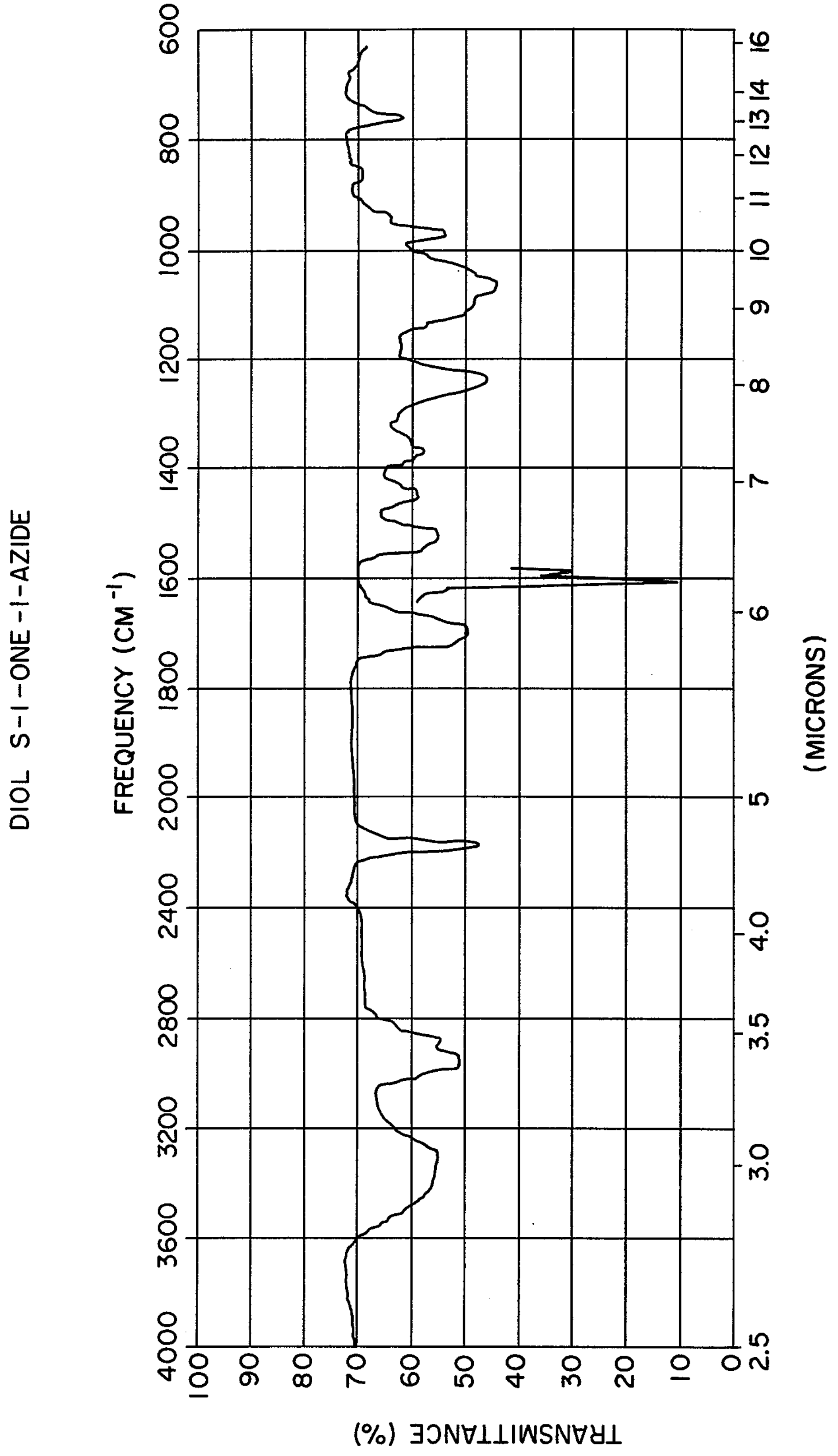
FIG. 1 depicts the infrared spectrum of diol S-1-one-1-azide.
Figure 2:
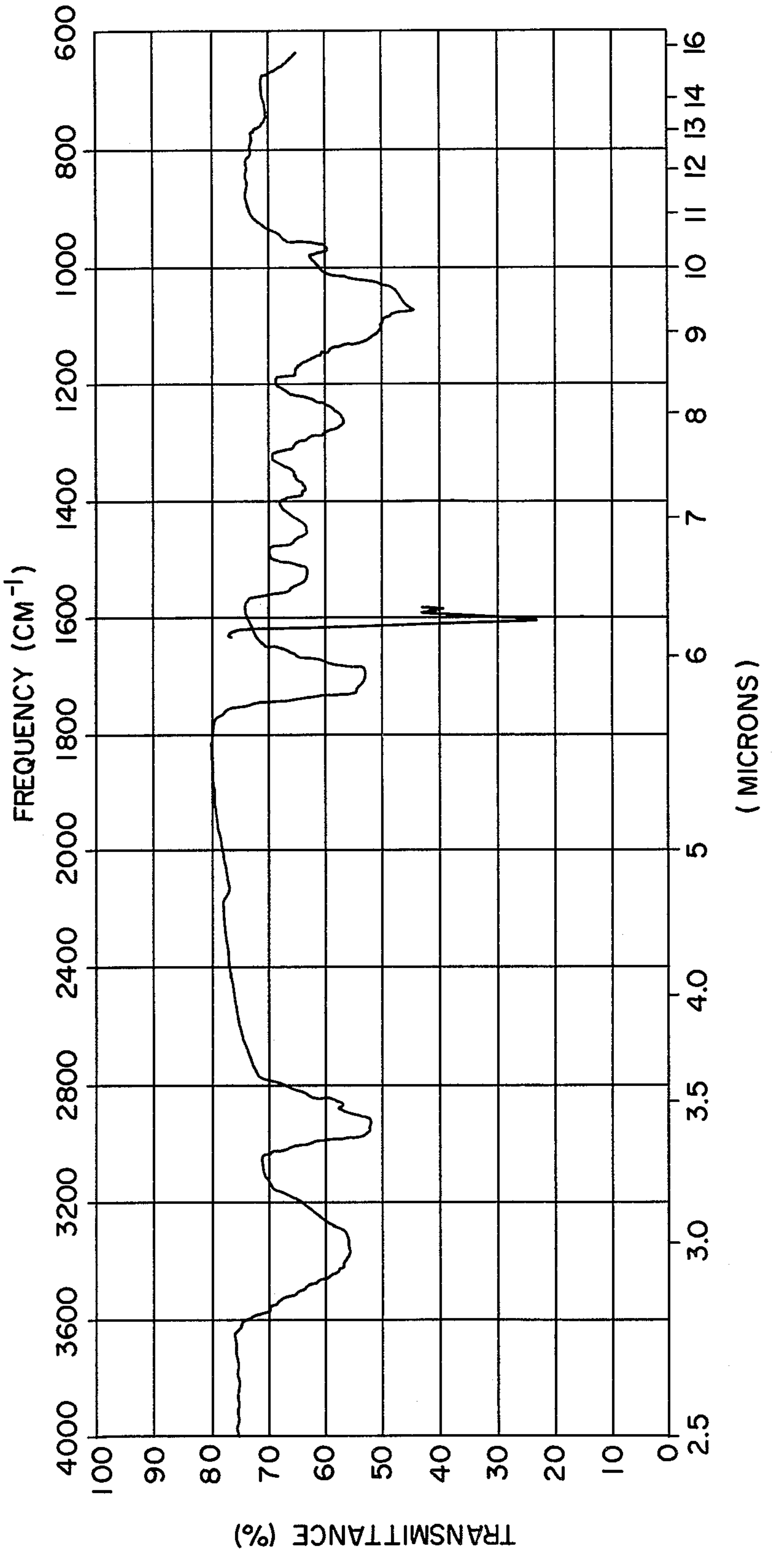
FIG. 2 depicts the infrared spectrum of 1-nor-2-aminodiol S ethyl carbamate.
Figure 3:
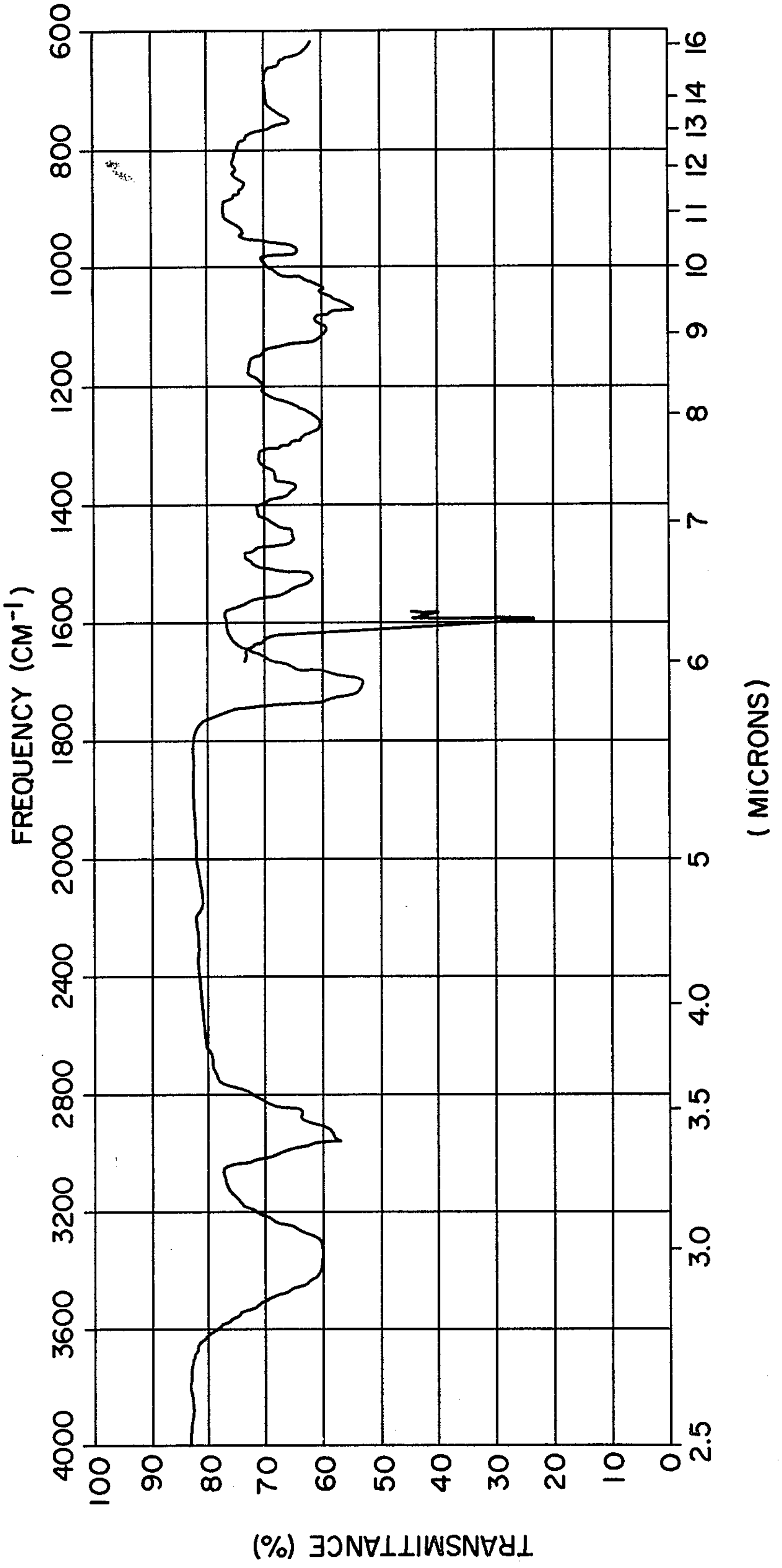
FIG. 3 depicts the infrared spectrum of 1-nor-2-aminodiol S methyl carbamate.
Figure 4:
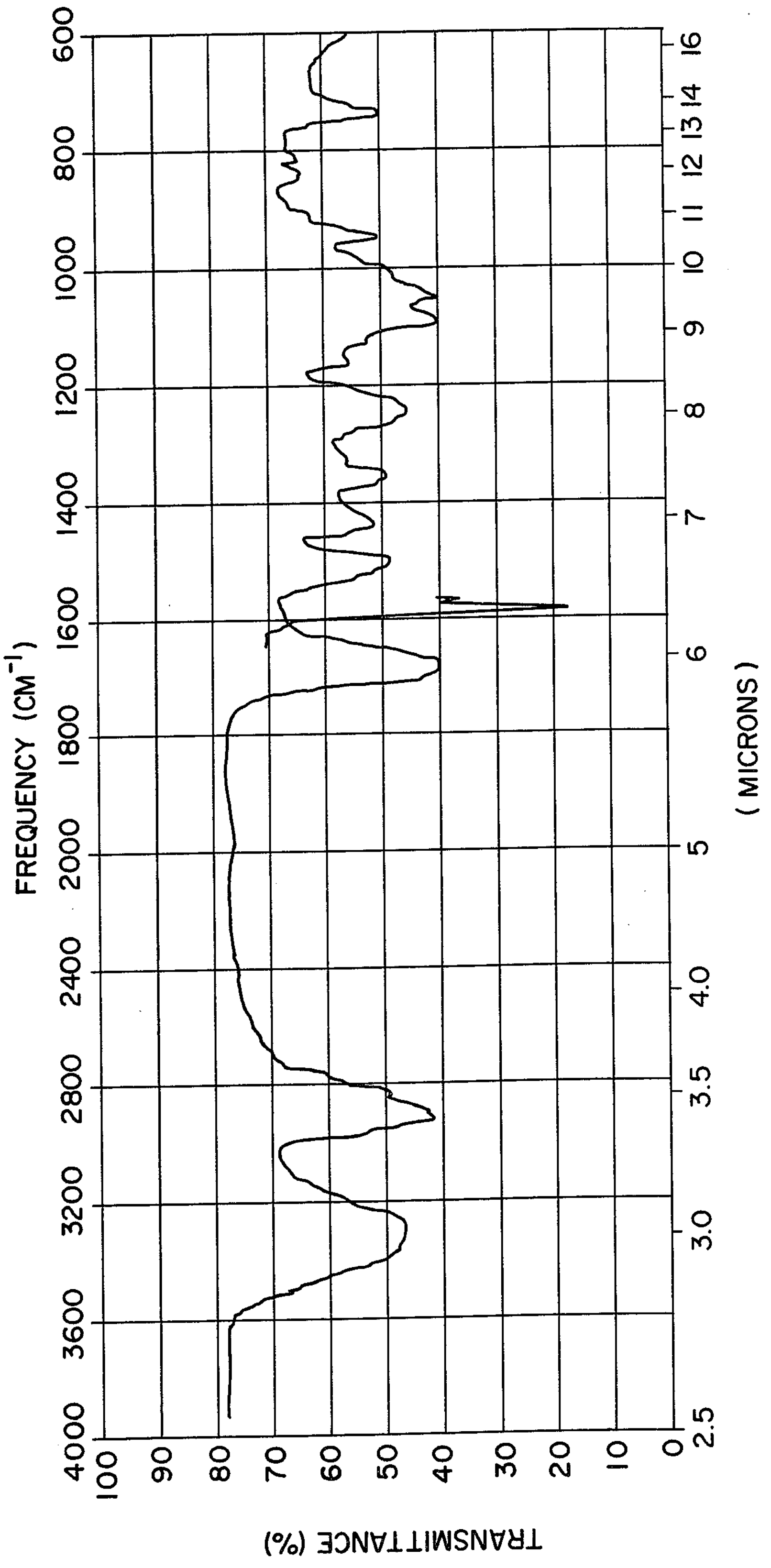
FIG. 4 depicts the infrared spectrum of 1-nor-2-aminodiol S isopropyl carbamate.
Figure 5:
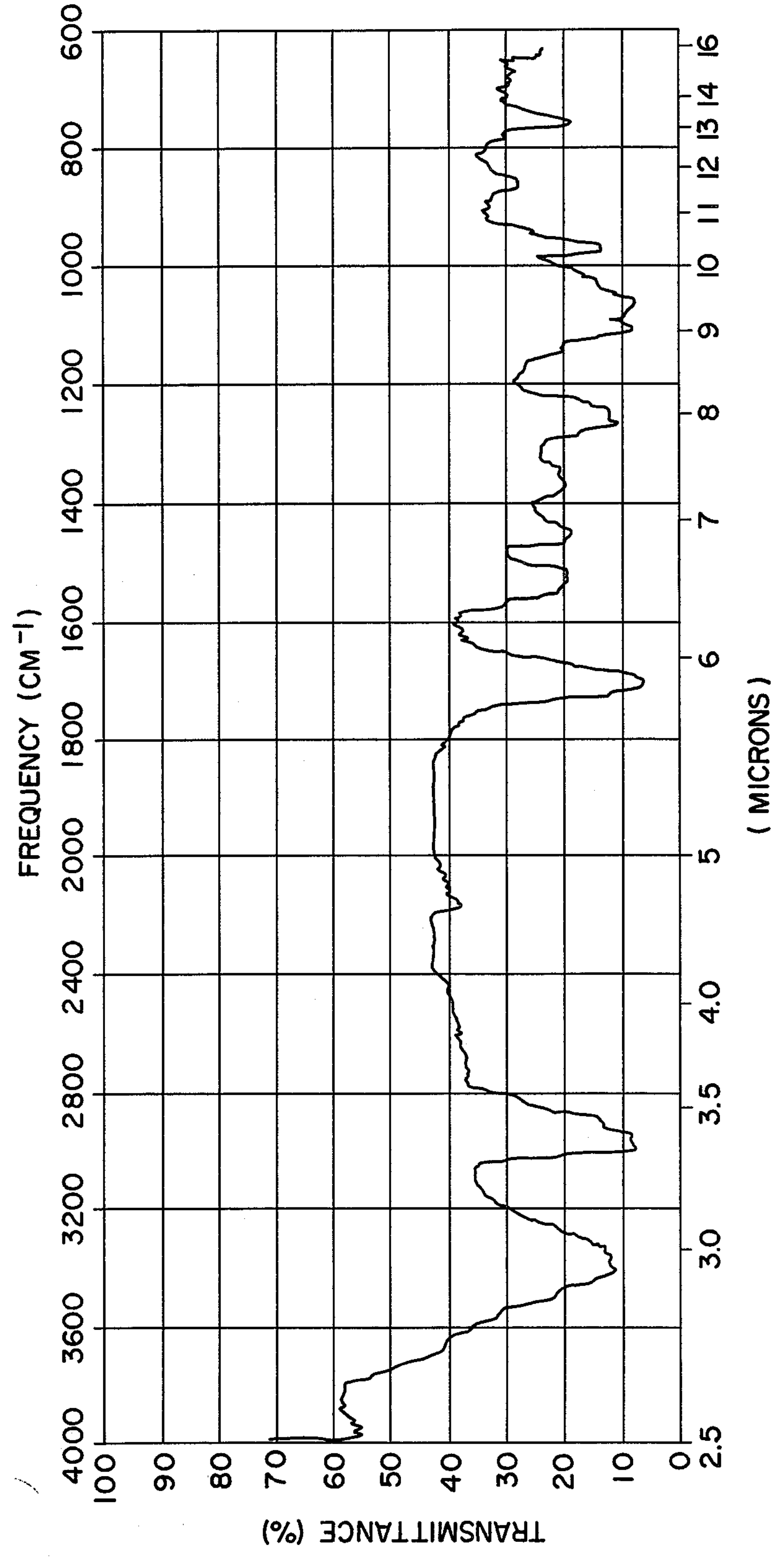
FIG. 5 depicts the infrared spectrum of 1-nor-2-aminodiol S n-propyl carbamate.

Diol S-1-one-1-Azide (III) was shown to have an azide structure by the characteristic azide band at 2170 in the infrared spectrum (depicted in FIG. 1 of the drawings) even though the highest observed ion in the mass spectrum was a M-28 peak (loss of $N_2$). This indicates a rearrangement of the Diol S-1-one-1-Azide (III) in the mass spectrometer to the corresponding isocyanate, R $C^2H_2NC^1O$, with R being the remaining part of the acid S molecule.

The Diol S-1-one-1-Azide is converted to the 1-nor-2 amino carbamates of this invention by refluxing one equivalent of the Diol S-1-one-1-Azide with an excess of an appropriate lower alkanol until the reaction is complete. Typically, from about 500 to about 2,000 equivalents of a lower alkanol having from 1 to 7 carbon atoms in a straight or a branched chain (preferably 1 to 4 carbon atoms are used with the proviso that the 4 carbon alkyl chain is n-butyl, isobutyl or secondary butyl. The reaction is conducted at reflux temperature for from about 6 hours to about 30 hours, using thin-layer chromatography to indicate completion of the reaction. Preferably the reaction is conducted in an inert atmosphere, i.e., under nitrogen, but this is not critical. No reaction takes place when t-butanol is used even after prolonged refluxing. Thus, the 1-nor-2-amino diol S alkyl carbamates of this invention having the following structure are obtained I:

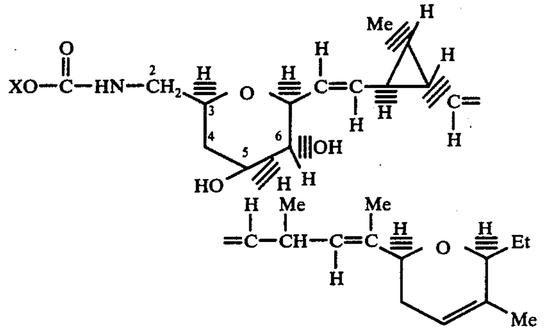

I wherein X represents an alkyl group having from 1 to 7 carbon atoms in a straight or a branched chain (preferably 1 to 4 carbon atoms), with the proviso that the 4 carbon alkyl group is n-butyl, isobutyl or secondary butyl.

In order to demonstrate that the 1-nor-2-amino diol S alkyl carbamates of this invention retain the two original hydroxyl groups at positions 5 and 6 in the acid S molecule and to demonstrate that no other reactions take place other than the above described transformation, the ethylcarbamate was converted to the corresponding diacetate with acetic anhydride and pyridine. Specifically, one equivalent of 1-nor-2-amino diol S ethylcarbamate having the empirical formula $C_{30}H_{47}NO_6$ and represented by the following formula:

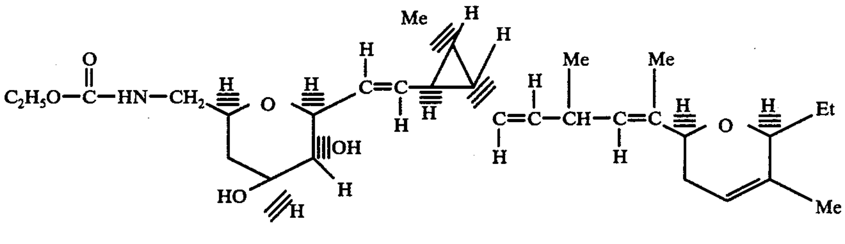

is reacted with from about 100 to about 2,000 (preferably 200) equivalents of acetic anhydride in from about 200 to about 4,000 (preferably about 400) equivalents of pyridine at room temperature. The reaction mixture is allowed to stand overnight, typically for from about 12 hours to about 20 hours, preferably for about 16 hours. Upon completion of the reaction, the 1-nor-2-amino diol S ethylcarbamate acetate, having the empirical formula $C_{34}H_{51}NO_8$ and represented by the following formula, is obtained:

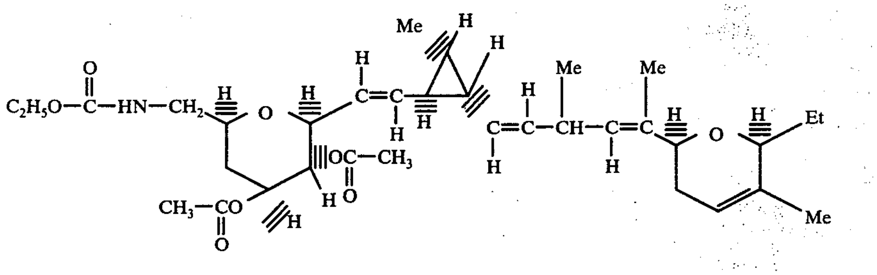

Figure 6:
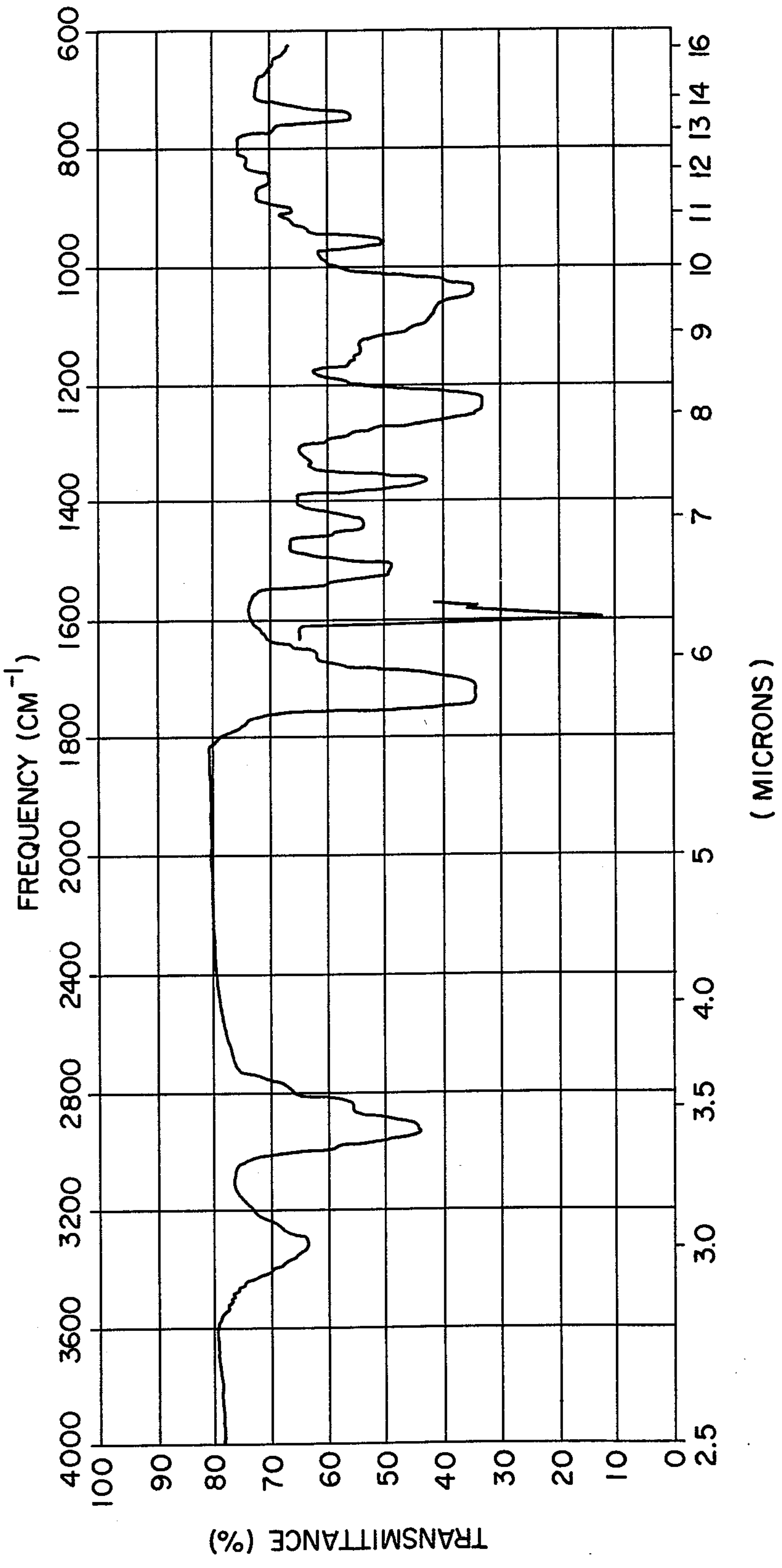
FIG. 6 depicts the infrared spectrum of 1-nor-2-aminodiol S ethyl carbamate diacetate.

The mass spectrum of this diacetate showed the correct molecular ion at 601 and the infrared spectrum (depicted in FIG. 6 of the drawings) showed the characteristic acetate carbonyl band at 1735cm$^{-1}$.

The 1-nor-2-amino carbamates of this invention derived from acid S are characterized by infrared spectroscopy and mass spectrometry.

The infrared spectra of the 1-nor-2-amino carbamate derivatives of acid S of this invention are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

The mass spectra of the 1-nor-2-amino carbamates of this invention derived from acid S are measured on a doublefocusing high resolution mass spectrometer utilizing a heated direct insertion probe. The molecular composition of the parent peaks are determined by employing perfluorotributylamine (mass spectral grade, available from PCR, Inc., Gainsville, Fla.) as the internal standard and peak matching techniques well-known to those skilled in the art. The application of these mass sepctral techniques permits not only the determination of the molecular composition of the parent ion and confirmation of the postulated transformations, but, like the aforementioned infrared measurements, provides a definitive physical property useful for identification purposes.

The novel 1-nor-2-amino carbamate derivatives of acid S of this invention inhibit the growth of a variety of fungi, including *Histoplasma capsulatum* and *Microsporum fulvum.* Minimum inhibitory concentrations falling within the range of from 1.56 to 0.049 micrograms/milliliter are obtained when evaluated by the in vitro tube dilution technique described in U.S. Pat. No. 3,651,216. Thus, the compounds of the present invention are useful in the treatment of dermatophytic and systemic fungal diseases.

The novel antifungal substances of this invention can be formulated with inert excipients into various dosage forms for oral parenteral and topical administration by methods well-known to those skilled in the pharmacist's art. Tablets, capsules, powders, solutions, suspensions, ointments, gels and creams are included among these dosage forms.

The 1-nor-2-amino carbamate derivatives of acid S of this invention can be administered orally, parenterally or topically to various mammals, such as dogs, cats and guinea pigs, afflicted with fungal diseases. The effective dosage range is about 0.01 to about 100 mg/kg of body weight for the treatment of a fungal disease.

The following examples are included to further illustrate the invention but are not to be construed as limiting the scope of the invention.

EXAMPLE 1

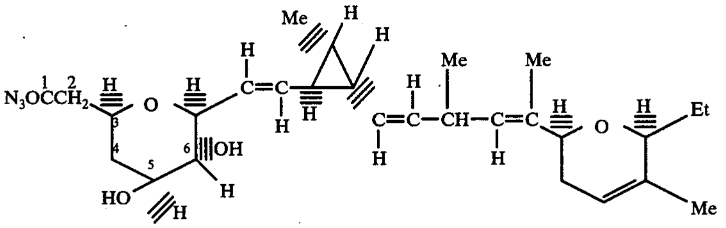

Diol S-1-one-1-azide. A solution of acid S (200 mg), diphenylphosphonic azide (300 mg) and triethylamine (100 mg) in t-butanol (25 ml) is refluxed under nitrogen for 6 hours. The solvents are removed under reduced pressure to give a brown oil. The product is purified by preparative thin-layer chromatography to give a colorless oil (150 mg, 74%). Diagnostic thin-lay chromatography indicates a pure homogeneous product.

Empirical formula: $C_{28}H_{41}N_3O_5$

Molecular weight: 499

Infrared Spectrum: $\nu$ max 3500–3200cm$^{-1}$ (OH), 2170 (azide), 1700 (C = O)

Mass Spectrum: m/e 471, 442 471 peak corresponds to $C_{28}H_{41}NO_5$, $[M^+-28]$

EXAMPLE 2

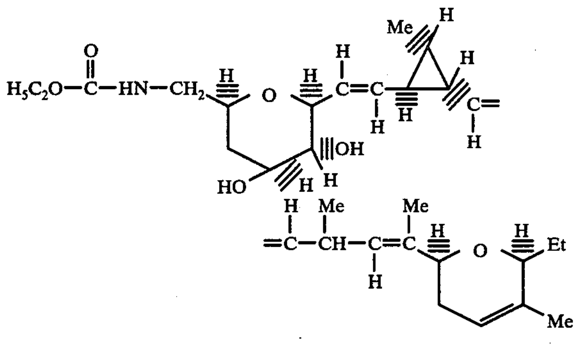

L-Nor-2-aminodiol S ethyl carbamate. A solution of diol S-1-one-1-azide (120 mg) in absolute ethanol (10 ml) is refluxed under nitrogen for 10 hours (thin-layer chromatography indicated complete reaction). The solvent is removed under reduced pressure to give a colorless oil. The oil is purified by preparative thin-layer chromatography to give a colorless gum (100 mg, 80%). Diagnostic thin-lay chromatography indicates a pure homogeneous product.

Empirical formula: $C_{30}H_{47}NO_6$
Molecular weight: 517
Infrared Spectrum: $\nu$ max 3500–3200cm$^{-1}$ (OH and NH), 1700cm$^{-1}$ (C = O)
Mass Spectrum: observed molecular ion 517.3402 calculated for $C_{30}H_{47}NO_6$ 517.3314
m/e (relative intensity) 517 (5), 499 (5), 488 (15), 422 (15) and 193 (100)

EXAMPLE 3

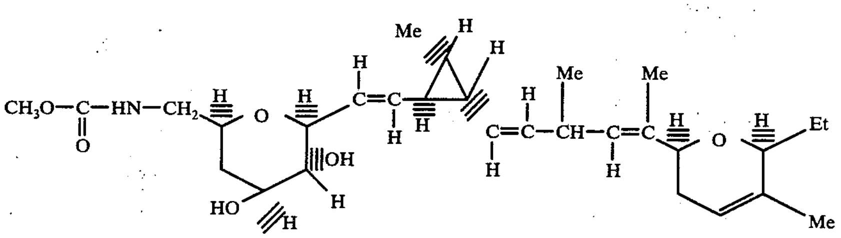

1-Nor-2-aminodiol S methyl carbamate. A solution of diol S-1-one-1-azide (33 mg) in methanol (10 ml) is refluxed under nitrogen for 16 hours. The product is obtained as a colorless gum (8 mg, 24%) by the general method described in Example 2. Diagnostic thin-layer chromatography indicates a pure homogeneous product.

Empirical formula: $C_{29}H_{45}NO_6$
Molecular weight: 503
Infrared Spectrum: $\nu$ max 3500–3200cm$^{-1}$ (OH and NH), 1700 (C = O)
Mass Spectrum: observed molecular ion 503.3188 calculated for $C_{29}H_{45}NO_6$ 503.3247
m/e (relative intensity) 503 (9), 485 (4), 474 (18), 408 (16) and 193 (100)

EXAMPLE 4

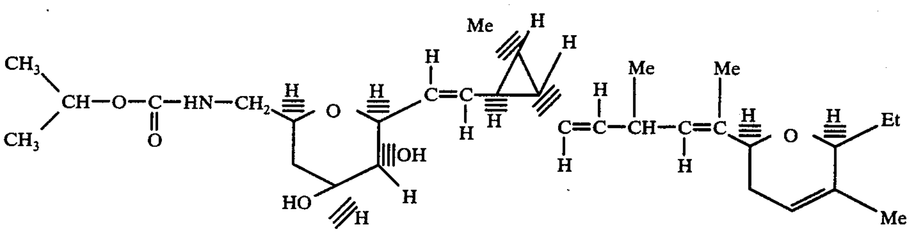

1-Nor-2-aminodiol S isopropylcarbamate. A solution of diol S-1-one-1-azide (15 mg) in isopropanol (5 ml) is refluxed under nitrogen for 26 hours. The product is obtained as a colorless oil (13 mg, 81%) by the general method described in Example 2. Diagnostic thin-layer chromatography indicates a pure homogeneous product.

Empirical formula: $C_{31}H_{49}NO_6$
Molecular weight: 531
Infrared Spectrum: $\nu$ max 3500–3200cm$^{-1}$ (OH and NH), 1700 (C = O)
Mass Spectrum: observed molecular ion 531.3487 calculated for $C_{31}H_{49}NO_6$ 531.3560
m/e (relative intensity) 531 (7), 513 (5), 502 (16), 436 (16) and 193 (100).

EXAMPLE 5

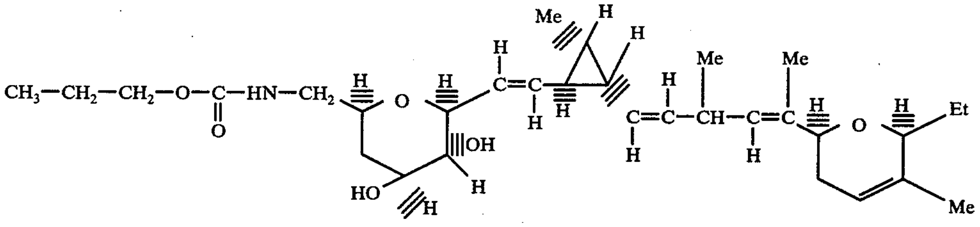

1-Nor-2-aminodiol S n-propyl carbamate. A solution of diol S-1-one-1-azide (40 mg) in n-propanol (5 ml) is refluxed under nitrogen for 6 hours. The product is obtained as a colorless oil (40 mg, 95%) by the general procedure described in Example 2. Diagnostic thin-layer chromatography indicates a pure homogeneous product.

Empirical formula: $C_{31}H_{49}NO_6$
Molecular weight: 531
Infrared Spectrum: $\nu$ max 3500–3200cm$^{-1}$ (OH and NH), 1700 (C = O)
Mass Spectrum: observed molecular ion 531.3594 calculated for $C_{31}H_{49}NO_6$ 531.3560
m/e (relative intensity) 531 (10), 513 (7), 502 (15), 436 (15) and 193 (100).

EXAMPLE 6

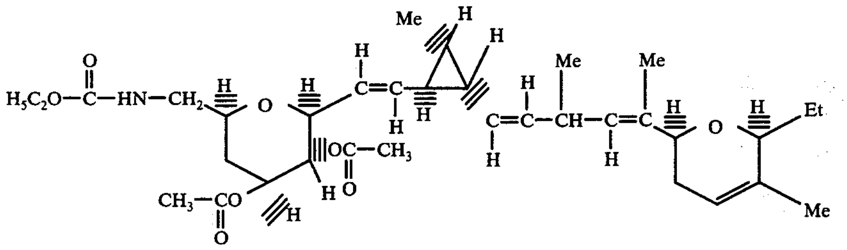

1-Nor-2-aminodiol S ethyl carbamate diacetate. 1-Nor-2-aminodiol S ethyl carbamate (34 mg) is dissolved in acetic anhydride (1 ml) and pyridine (2 ml). The solution is allowed to stand at room temperature overnight. The excess acetic anhydride is decomposed with methanol and the solvents are removed under reduced pressure to give the crude product. Purification by preparative thin-layer chromatography gives a colorless oil (36 mg, 90%). Diagnostic thin-layer chromatography indicates a pure homogeneous product.

Empirical formula: $C_{34}H_{51}NO_8$

Molecular weight: 601

Infrared Spectrum: $\nu$ max 3325cm$^{-1}$ (N—H), 1735 (C = O of acetates) 1700 (CO of carbamate)

Mass Spectrum: Molecular ion at 601 corresponding to $C_{34}H_{51}NO_8$ m/e 601, 583, 572, 506, 193

I claim:

1. A compound having the formula I:

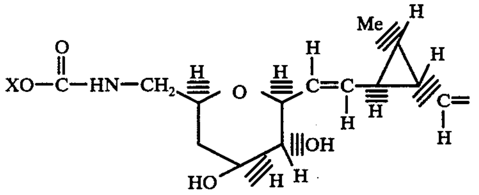

I

-continued

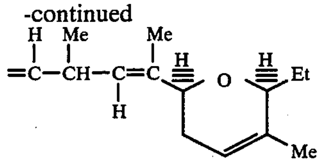

wherein X is lower alkyl with the proviso that the 4-carbon alkyl group is n-butyl, isobutyl or secondary butyl.

2. A compound according to claim 1 which has the formula:

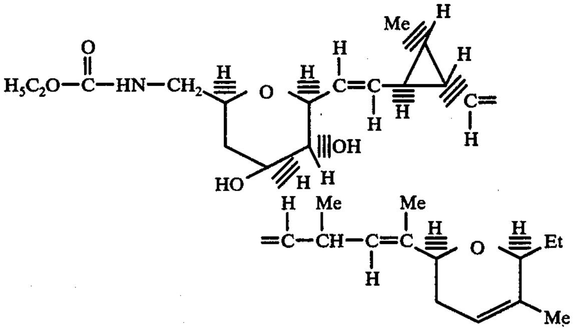

3. A compound according to claim 1 which has the formula:

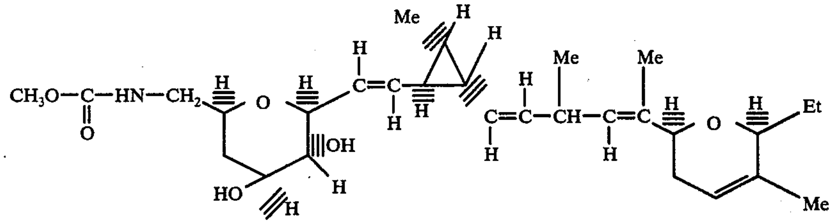

4. A compound according to claim 1 which has the formula:

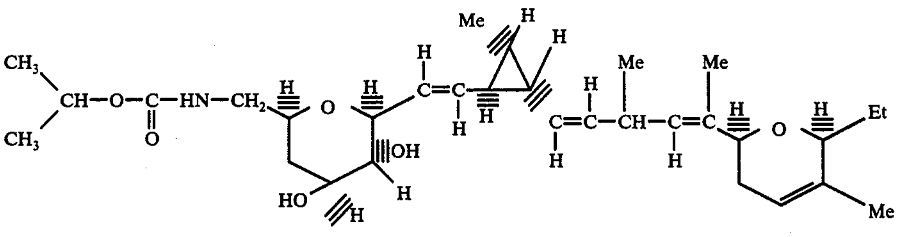

5. A compound according to claim 1 which has the formula:

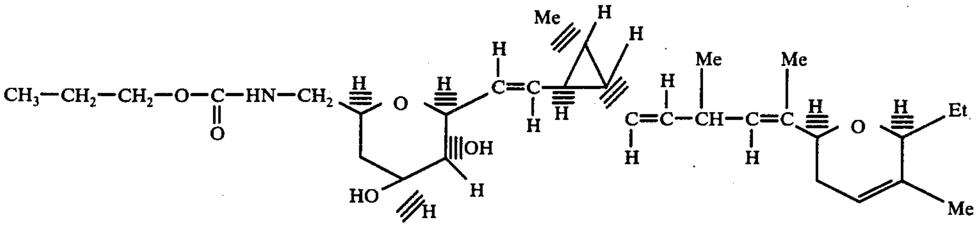

6. A compound having the formula:

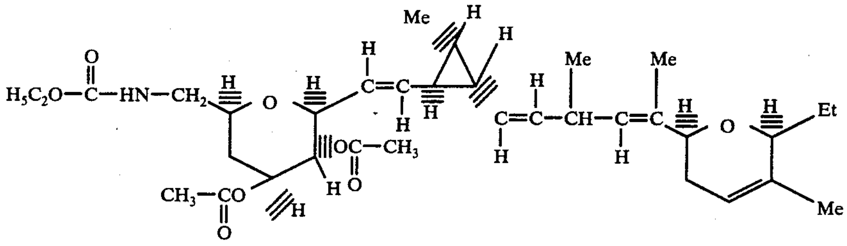

7. A compound having the formula:

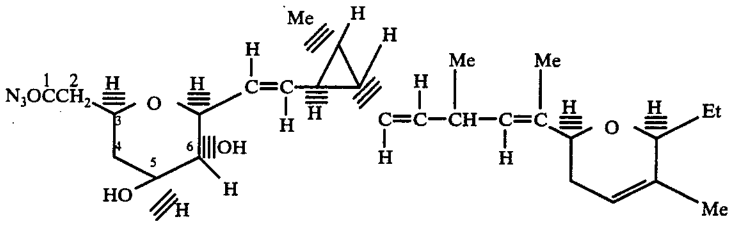

8. A process for preparing a compound, Diol-S-1-one-1-azide having the empirical formula $C_{28}H_{41}N_3O_5$ and represented by the formula:

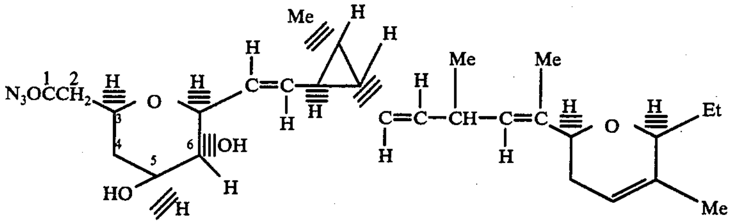

which comprises reacting one equivalent of acid S having the empirical formula $C_{28}H_{42}O_6$ and represented by the following formula:

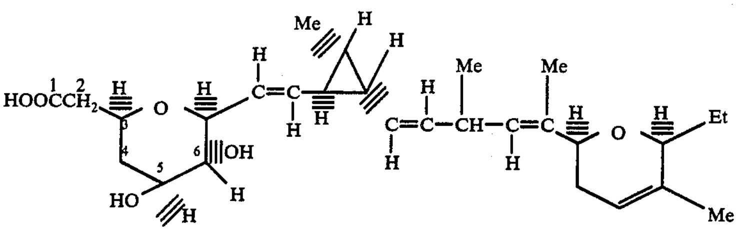

with from about 2.5 to 3 equivalents of diphenylphosphonic azide and from about 2.5 to about 3 equivalents of triethyl amine in from about 100 to about 300 equivalents of t-butanol at reflux temperature for from about 5 to about 24 hours.

9. A process for a compound, 1-nor-2-aminodiol S alkylcarbamate, having the formula I:

I

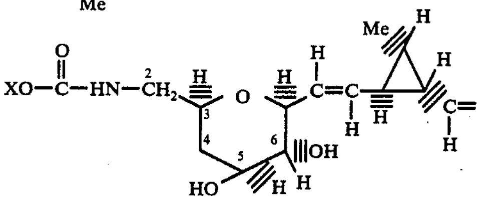

-continued

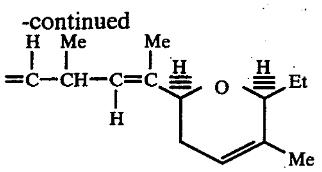

wherein X represents a 1 to 7 carbon straight or branched chain alkyl group, with the proviso that the 4 carbon alkyl group is n-butyl, isobutyl or secondary butyl; which comprises reacting one equivalent of Diol S-1-one-1-azide, having the empirical formula $C_{28}H_{41}N_3O_5$ and prepresented by the following structure:

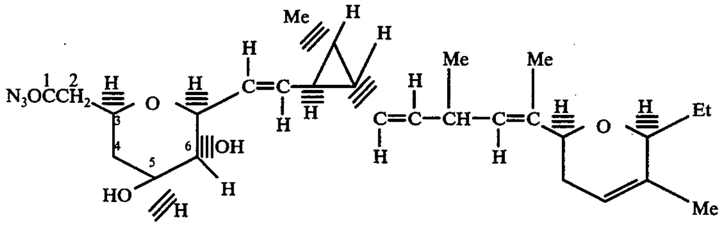

with from about 500 to about 2,000 equivalents of a lower alkanol having from 1 to 7 carbon atoms in a straight or branched alkyl chain, with the provisio that the 4 carbon alkyl chain is n-butyl, isobutyl or secondary butyl, at reflux temperature for from about six to about thirty hours.

10. A process according to claim 9 wherein X is a 1 to 4 carbon straight or branched alkyl chain with the proviso that the 4 carbon alkyl chain is n-butyl, isobutyl or secondary butyl and the lower alkanol has from 1 to 4 carbons in the straight or branched alkyl chain with the proviso that the 4 carbon alkyl chain is n-butyl, isobutyl or secondary butyl.

11. A process for preparing the compound, 1-nor-2-aminodiol S ethylcarbamate diacetate, having the empirical formula $C_{34}H_{51}NO_8$ and the following structural formula:

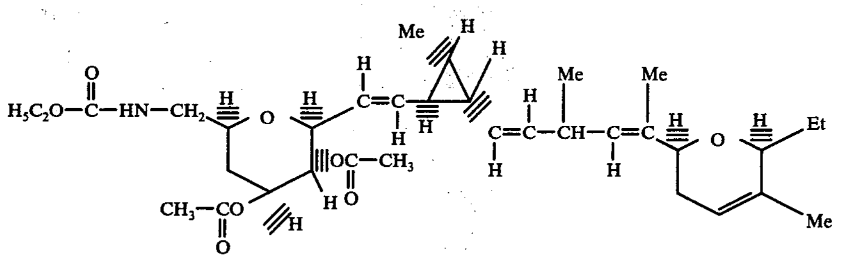

which comprises reacting one equivalent of 1-nor-2-aminodiol S ethylcarbamate, having the empirical formula $C_{30}H_{47}NO_6$ and the following structural formula:

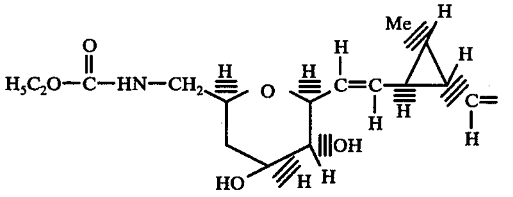

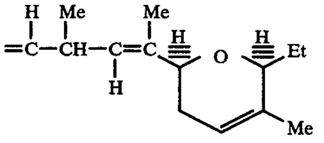

with from about 100 to about 2,000 equivalents of acetic anhydride, in from about 200 to about 4,000 equivalents of pyridine at room temperature for from about 12 hours to about 20 hours.

* * * * *